(12) United States Patent
Bodily et al.

(10) Patent No.: US 8,272,279 B2
(45) Date of Patent: Sep. 25, 2012

(54) SYSTEMS AND METHODS FOR CHEMICAL SAMPLING IN PARTICULATE LADEN GASEOUS ENVIRONMENTS

(75) Inventors: Gary R. Bodily, North Logan, UT (US); Neil Arnold, Sandy, UT (US); Jed W. Bodily, North Salt Lake, UT (US); Daniel C. Maxwell, West Valley City, UT (US)

(73) Assignee: Seer Technology, Inc., Salt Lake City, UT (US)

( * ) Notice: Subject to any disclaimer, the term of this patent is extended or adjusted under 35 U.S.C. 154(b) by 478 days.

(21) Appl. No.: 12/504,589

(22) Filed: Jul. 16, 2009

(65) Prior Publication Data

US 2011/0011158 A1    Jan. 20, 2011

(51) Int. Cl.
*G01N 1/22* (2006.01)
*G01N 1/24* (2006.01)

(52) U.S. Cl. ............... 73/863.23; 73/863.21; 73/863.71; 73/864.71

(58) Field of Classification Search ............... 73/863, 73/863.11, 863.12, 863.21–863.23, 863.71, 73/864.71

See application file for complete search history.

(56) References Cited

U.S. PATENT DOCUMENTS

| | | | |
|---|---|---|---|
| 5,163,332 A * | 11/1992 | Wong ......................... | 73/863.23 |
| 5,889,199 A * | 3/1999 | Wong et al. ....................... | 73/40 |
| 7,240,546 B2 | 7/2007 | DiFoggio | |
| 7,243,560 B2 * | 7/2007 | Coyle et al. ................. | 73/863.22 |
| 7,377,188 B2 * | 5/2008 | Jenkins ....................... | 73/863.23 |
| 7,387,764 B2 * | 6/2008 | Uchihara et al. ................. | 422/80 |
| 7,799,567 B1 * | 9/2010 | Call ................................ | 436/53 |
| 2003/0033890 A1 * | 2/2003 | Rodgers ..................... | 73/863.43 |
| 2003/0115975 A1 * | 6/2003 | Saaski et al. ................ | 73/864.33 |
| 2004/0154414 A1 * | 8/2004 | LaCourse et al. .......... | 73/863.23 |
| 2005/0076722 A1 * | 4/2005 | Strohmeyer et al. ....... | 73/863.83 |
| 2005/0274206 A1 * | 12/2005 | Coyle et al. ................. | 73/864.71 |
| 2006/0042407 A1 * | 3/2006 | Napoli ........................ | 73/863.12 |
| 2007/0186696 A1 * | 8/2007 | Pletcher et al. ............ | 73/864.71 |
| 2009/0020696 A1 * | 1/2009 | Bier ............................... | 250/288 |

* cited by examiner

*Primary Examiner* — David Rogers

(74) *Attorney, Agent, or Firm* — Thorpe North & Western LLP

(57) ABSTRACT

Chemical sampling systems and methods that can inexpensively and efficiently provide accurate chemical sampling in dusty environments are disclosed. The system can include a chemical detector, an elastomeric membrane, and a support structure for the elastomeric membrane. The gas chromatograph can have a sample inlet through which chemicals from the gaseous environment can enter the gas chromatograph. The sample inlet can be covered with the elastomeric membrane, the elastomeric membrane being configured to extract chemicals from the gaseous environment while excluding dust and other particles from passing into the gas chromatograph. The support structure can be disposed between the elastomeric membrane and the sample inlet and can provide mechanical support to the elastomeric membrane.

19 Claims, 3 Drawing Sheets

SYSTEMS AND METHODS FOR CHEMICAL SAMPLING IN PARTICULATE LADEN GASEOUS ENVIRONMENTS

FIELD OF THE INVENTION

The present invention relates generally to chemical detection systems and methods. More particularly, the present invention relates to dust filtration in chemical detection systems.

BACKGROUND

It is frequently necessary to sample gaseous chemicals present in dirty and dusty environments. Dust present in an environment can be extremely fine, often smaller than 50 microns. Dust and dirt smaller than 50 microns can be suspended in the air for a long time. The dust can inhibit or prevent the accurate sampling and identification of chemicals present in the environment. Numerous technologies have been developed in order to try to combat the problems associated with chemical sampling in dusty environments. Most technologies available to combat dust involve the removal of the dust from the air. Examples of such technologies include HEPA filters, impactors, and cyclone systems. Each of these technologies suffers from shortcomings. For example, HEPA filters tend to clog and require frequent and costly replacement. The clogging of the HEPA filter can be unpredictable, inconvenient, and cost prohibitive to a chemical sampling operation. Impactors and cyclone systems do not clog, however their dust removal efficiency is lower then HEPA filters and small particles of dust are frequently left in the air. These small particles can cause long-term damage to testing equipment systems and distortions of, or inaccuracies in, the sampling data.

SUMMARY OF THE INVENTION

In light of the foregoing, the Applicants have recognized a need to develop chemical sampling systems and methods that can inexpensively and efficiently provide accurate chemical sampling in dusty environments. Accordingly, the present application provides for a system for sampling chemicals in a gaseous environment, particularly one in which dust is present. The system can include a point chemical detector, an elastomeric membrane, and a support structure for the elastomeric membrane. The chemical detector can have a sample inlet through which chemicals from the gaseous environment can enter the gas chromatograph. The elastomeric membrane can be disposed between the sample inlet and the gaseous environment. The elastomeric membrane can be configured to allow passage of chemicals from the gaseous environment while excluding dust and other particles from passing into the gas chromatograph. A support structure can be disposed between the elastomeric membrane and the sample inlet and can provide mechanical support to the elastomeric membrane.

In another embodiment, a method of measuring atmospheric chemical composition is disclosed. A chemical sampling system, such as described above, is used in the method. The method includes the steps of disposing a chemical sampling system in or near an environment needed to be tested, contacting the elastomeric membrane in the sampling system with air from the environment, regulating the passage of chemicals present in air through the elastomeric membrane and the sample inlet and into the chemical sampling device, and identifying the chemicals using the chemical sampling device.

BRIEF DESCRIPTION OF THE DRAWINGS

Additional features and advantages of the invention will be apparent from the detailed description which follows, taken in conjunction with the accompanying drawings, which together illustrate, by way of example, features of the invention.

Figure 1A:
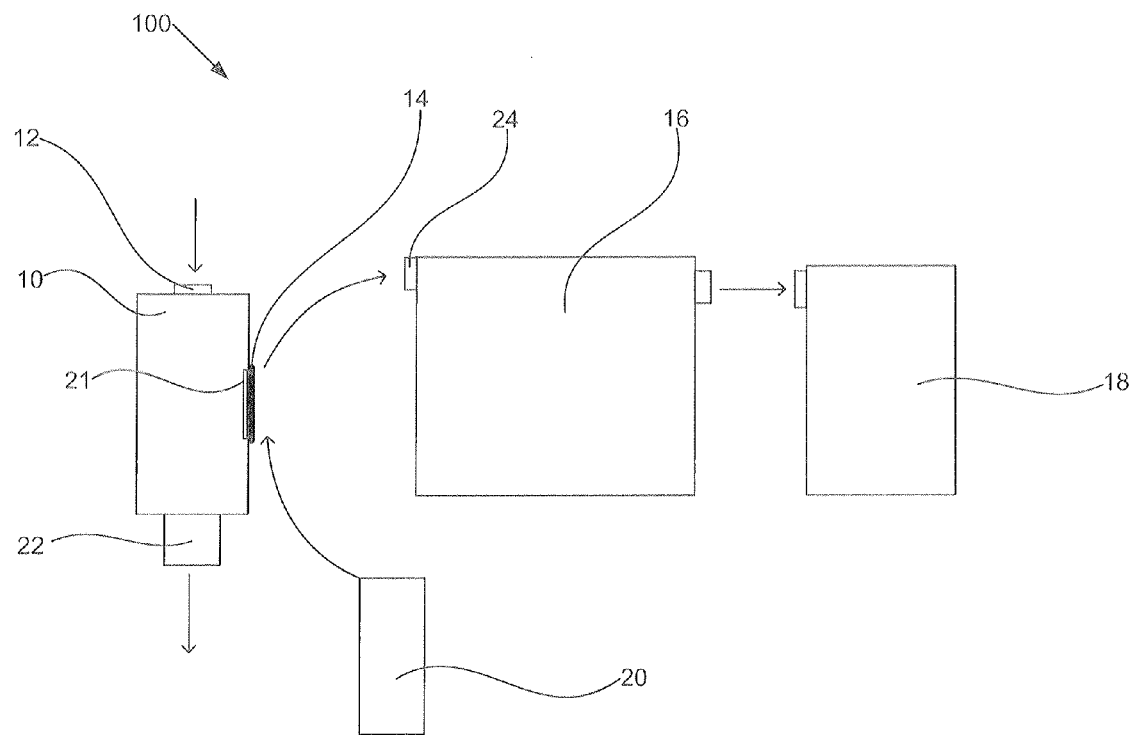
FIG. 1a is a schematic diagram of one embodiment of the system of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting. The scope of the present invention will be defined only by the appended claims and equivalents thereof.

In describing and claiming the present invention, the following terminology will be used.

The singular forms "a", "an", and "the" include plural referents unless the context clearly dictates otherwise. Thus, for example, reference to "a chemical" includes reference to one or more of such chemicals.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described.

The described features, structures, or characteristics described herein may be combined in any suitable manner in one or more embodiments. Furthermore, one skilled in the relevant art will recognize that the invention can be practiced without one or more of the specific details, methods, components, materials, etc. In other instances, well-known components, methods, structures, and materials may not be shown or described in detail to avoid obscuring aspects of the invention.

Throughout this disclosure, the term "dust" is used to represent a contaminant in the system for sampling chemicals. Other materials may be present within the system including fibers, hair, water, other liquids, or any material that is not a vapor or gas in nature. The term dust, as used in the disclosure, is intended to refer to all of these materials.

With this background in mind, the present disclosure is drawn to a system for sampling chemicals in a gaseous environment, particularly one in which dust is present. The system can include a chemical sampling device, also referred to herein as a chemical detector. The chemical sampling device can be a point chemical detector that includes a sample inlet, such as a gas chromatograph, an ion mobility spectrometer, a mass spectrometer, a Raman spectrometer, and the like. The system can further comprise an elastomeric membrane and a support structure for the elastomeric membrane. The chemical sampling device can have a sample inlet through which chemicals from the gaseous environment can enter the gas chromatograph. The elastomeric membrane can be disposed between the sample inlet and the gaseous environment, the elastomeric membrane being configured to allow transfer of chemicals from the gaseous environment into the gas chromatograph while excluding dust and other particles. A support structure can be disposed between the elastomeric membrane and the sample inlet and can provide mechanical support to the elastomeric membrane.

FIG. 1a shows a schematic diagram of one embodiment of a system for sampling chemicals in a gaseous environment per the present application. The system 100 includes an air inlet 10 having an intake port 12 through which air enters the air inlet and an exhaust port 22 through which air leaves the air inlet. As shown, an elastomeric membrane 14 is incorporated into the wall of the air inlet. The elastomeric membrane acts to exclude dust and other particles from entering the sample inlet 24 of a chemical detector 16 while permitting the passage of chemicals through the sample inlet and into the chemical detector. Once the chemicals pass through the elastomeric membrane they are carried into the sample inlet of the chemical detector. In one embodiment, the chemical detector can be a gas chromatograph that carries the chemicals into the sample inlet 24 using a gas mobile phase that is provided by a gas source 20. After passing through the column of the gas chromatograph, the chemicals are detected by a detector 18.

The passage of the air into the air inlet 12 can be passive or active. When the air movement is active, the system can include an air-moving component such as a fan or blower 22. In one embodiment, the air moving component can be disposed upstream of the inlet port of the air inlet and can force the air into the air inlet (not shown). In another embodiment, the air-moving component can be located downstream of the air inlet and can draw the air through the inlet port and into the air inlet. Placement of the air-moving component downstream of the air inlet can be advantageous when the air inlet includes a particle separator, such as the cyclone shown in FIG. 2. In such an embodiment, the particle separator can reduce the amount of particulates that reach the air-moving component, thereby increasing the lifespan and efficacy of the air-moving component.

Once the chemicals have passed through the elastomeric membrane they can pass through a sample inlet 24 and into a chemical sampling device 16. For the purposes of the present application, a "sample inlet" is defined as a component or series of components which facilitate the transfer of chemicals from the elastomeric membrane to the chemical sampling device. The sample inlet can be as simple or as complex as necessary to accomplish the defined task. Generally, the transfer of the chemicals from the elastomeric membrane to the sampling device can be aided by a mobile phase, such an inert gas, which carries the chemicals that transfer through the elastomeric membrane to and through the sampling device.

In one embodiment, the sample device 16 can be gas chromatograph. The type of column or columns used in the gas chromatograph may vary depending on the particular chemicals being sampled. A determination of which column(s) to use can be made by one of ordinary skill in the art. The sampling device may be used alone or in conjunction with any type of detector known in the art. Examples of chemical detectors include, but are not limited to, infrared detectors, mass-spectrometers, flame ionization detectors, thermal conductivity detectors, discharge ionization detectors, electron capture detectors, flame photometric detectors, Hall electrolytic conductivity detectors, helium ionization detectors, nitrogen phosphorus detectors, mass selective detectors, photo-ionization detectors, pulsed discharge ionization detectors, thermal energy(conductivity) analyzer/detectors, combinations thereof, and the like. It is understood that selection of the detector will vary depending on the nature and type of the chemicals being tested for. Non-limiting examples of chromatographic systems which can be used as the chemical sampling device include those described in U.S. patent application Ser. Nos. 11/765,383; 11/765,388; and 11/765,386, each of which is incorporated by reference herein in its entirety.

The present invention provides means for sampling the chemicals present in a gaseous environment without having to concentrate the air to increase the concentration of the chemicals therein. This is accomplished through the use of an elastomeric membrane that allows for the passage of chemicals while substantially inhibiting the passage of air. The elastomeric membranes of the present invention can be made of any elastomeric composition that allows for the passage, generally by diffusion, of chemicals from an air sample. Non-limiting examples of elastomeric compositions from which the elastomeric membrane can be made include silicone rubber, silastic, polyurethane, high-density foam, and combinations thereof. Generally, elastomeric compositions comprising rubber with a plasticizing content in the range of 20% to 60% can provide a useful elastomeric membrane.

In one embodiment, the elastomeric membrane can be made of silicone rubber. The thickness of the elastomeric membrane can vary depending on the desired rate of transfer of the chemicals and the type of material used for the membrane. In one embodiment, the elastomeric membrane can have a thickness of about 0.001 inches to about 1 inch. In another embodiment, the elastomeric membrane can have a thickness of about 0.001 inches to about 0.5 inches. A thinner membrane typically enables chemicals to diffuse through the membrane more rapidly than a thicker membrane. However, a thicker membrane can provide better structural support.

Figure 1B:
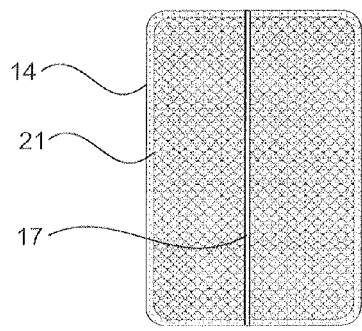
FIG. 1b is an illustration of a membrane supported by a support structure in accordance with an embodiment of the present invention.

The elastomeric membranes 14 of the present invention, as shown in the exemplary embodiment of FIG. 1a, can be supported in the system by a support structure 21, as illustrated in FIGS. 1a and 1b. Generally, the support structure 21 can be disposed between the elastomeric membrane and the sample inlet and can function to provide mechanical support to the elastomeric membrane. The support structure can be made of any material known in the art that can effectively retain and support the elastomeric membrane in its relationship with the rest of the system. The support structure is typically composed of materials that have a low interaction with chemicals that pass through the membrane 14. Non-limiting examples of materials from which the support structure can be made include stainless steel, ceramics, plastics, and combinations thereof. The support structure can be of any configuration that will effectively support the elastomeric membrane. For example, in one embodiment, the support structure can be a perforated material, such as a perforated metal screen, which is placed behind or on the sample inlet side of the elastomeric membrane. In another embodiment, the support structure can be a stainless steel metal plate having a plurality of holes to allow the chemicals that diffuse through the membrane to pass through to the sample inlet 24. The exact configuration and number of the perforations can be balanced so as to provide adequate support of the elastomeric membrane without substantially inhibiting the passage of chemicals through the membrane and into the sample inlet.

In some embodiments of the present application, it can be useful to control the temperature of the elastomeric membrane. The rate of passage or transfer of chemicals through the elastomeric membrane and into the sample inlet can be regulated by controlling the temperature of the membrane and or the temperature of the environment surrounding the elastomeric membrane. When the temperature of the elastomeric membrane is increased, the rate of transfer of chemicals through the membrane is also increased. Similarly, when the temperature of the membrane is decreased, the rate of transfer of chemicals through the membrane is also decreased. The ability to control the rate of transfer or passage of chemicals through the elastomeric membrane can be very useful, particularly when there is a desire for near real-time analysis of the chemicals present in the air. Similarly, the ability to cool the elastomeric membrane can prove helpful by inhibiting the passage of the chemicals through the membrane. When cooled, the membrane can act as a concentrator for the chemicals, collecting them on the surface of the membrane but inhibiting their passage until the temperature of the membrane is raised.

In accordance with the above discussion, the support structure 21 can be configured as a temperature-regulating device capable of heating and/or cooling the elastomeric membrane. In one embodiment, the support structure can be configured as a Peltier heater. The support structure itself can be constructed of a material that can be effectively heated or cooled using the Peltier effect. Alternatively, a separate material that uses the Peltier effect can be coupled to the support structure. In another embodiment, the support structure can include a resistive type heating device. The desired temperature of the support structure and membrane can vary depending on the desired transfer rate, the thickness of the elastomeric membrane, and the compositional make-up of the support structure and elastomeric membrane. Determination of appropriate temperatures for desired transfer rates is within the skill of those skilled in the art.

In one embodiment, the temperature of the elastomeric membrane can be regulated by heating, such as by the support structure, to a temperature of about 35° C. to about 500° C. In another embodiment, the temperature of the elastomeric membrane can be regulated by heating to a temperature of about 40° C. to about 230° C. Similarly, the temperature of the elastomeric membrane can be regulated by cooling to a temperature of about −100° C. to about 50° C. As would be understood by one of ordinary skill in the art, the need to heat or cool to a given temperature can be dictated by the temperature of the ambient air, i.e. cool environments may require greater heating while extremely hot environments may require little heating or even cooling to obtain desired transfer rates.

The systems of the present application can further include an air inlet 10 (FIG. 1a) that can be operably disposed between the elastomeric membrane and the gaseous environment. The air inlet can take a variety of forms. In one embodiment, the air inlet can include the membrane 14 and support structure 21. In another embodiment, the air inlet can be a chamber having an inlet port 12 through which gas from the environment is drawn in and an exhaust or outlet port 22 through which the gas can be expelled. The inlet and outlet ports can have differing sizes in order to facilitate desired intake velocities of the gas from the environment. For example, the inlet port can be smaller than the outlet port in order to generate high intake velocity. In one embodiment, the air inlet can be configured to allow for the passage of air over the elastomeric membrane 14 at a relatively high velocity. The passage of air over the elastomeric membrane at high velocities can enable the adherance of and the subsequent removal of a portion of dust or particulate matter on the elastomeric membrane.

Figure 2:
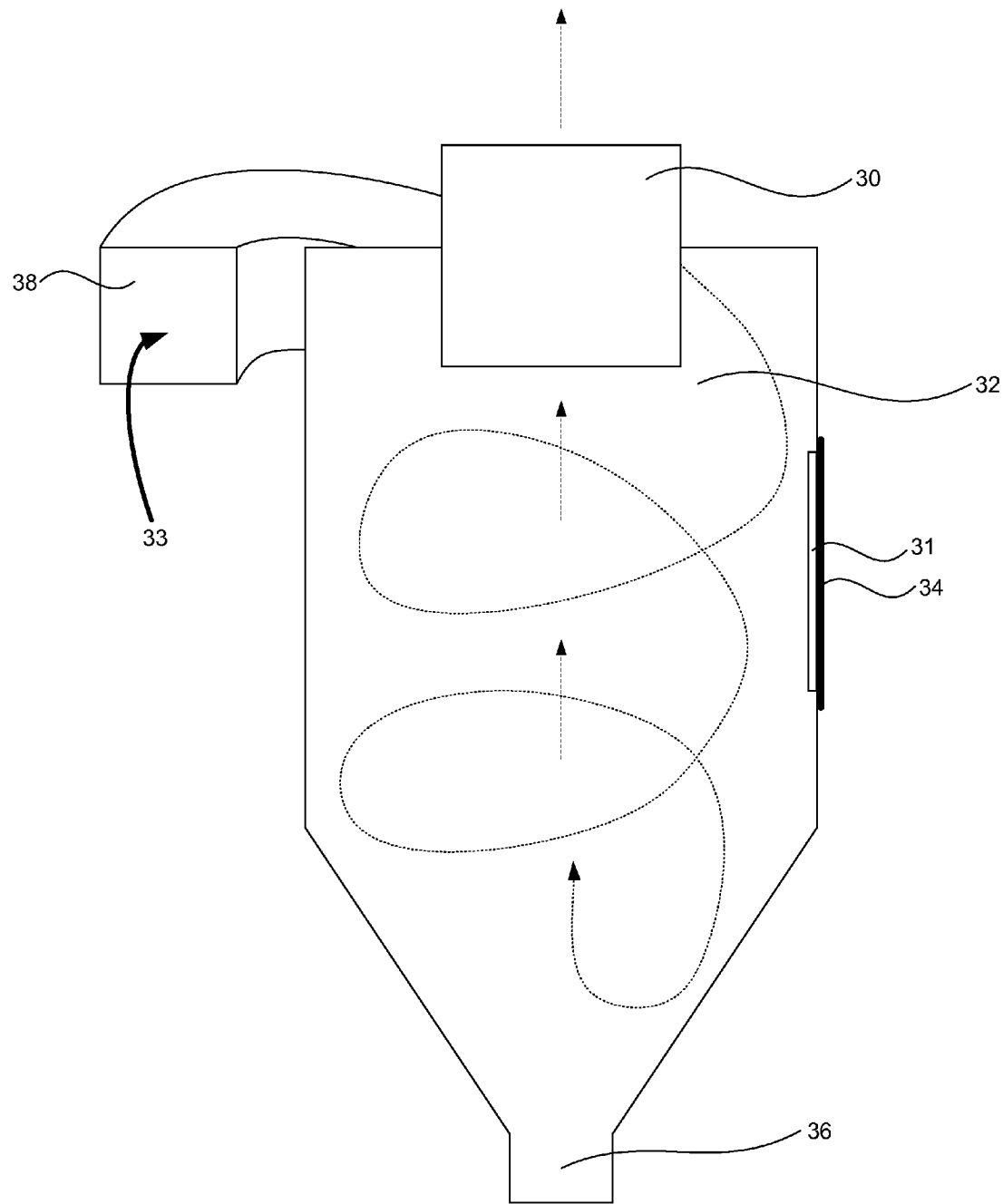
FIG. 2 is a cross-sectional view of one exemplary embodiment of a cyclone particle separator into which an elastomeric membrane of the present invention is integrated.

In another embodiment, the air inlet can be a component that aids in removing particulates from the air such as a cyclone particle separator. Cyclone particle separators are well known in the art as being capable of removing particulate matter, e.g. dust, from the air. Any type of cyclone particle separator known in the art can be used. FIG. 2 shows one example of a cyclone particle separator that can be used with the systems of the present application. Air 33 from an external environment is drawn through the inlet port 38 at a relatively high velocity. The air enters the cyclone chamber 32 in a circular motion and at high velocity. The centrifugal force created from the high velocity circling of the air causes particulates in the air to impact the walls of the cyclone and settle into the particle collector 36 located at the bottom of the cyclone chamber. The air can exit the cyclone through an exhaust port 30 in the top of the cyclone chamber.

In the embodiment shown in FIG. 2, an elastomeric membrane 34 and support structure 31 are integrated into the wall of the cyclone particle separator. As the air passes through the cyclone separator, chemicals present in the air can contact and diffuse through the elastomeric membrane and enter a chemical detector for sensing of the chemicals present in the air.

Although it can be desirable to remove dust from the air prior to its contact with the elastomeric membrane, such as through the use of a cyclone, some dust can still reach and contact the membrane. When dust does contact the elastomeric membrane, some of the dust may stick or adhere to the elastomeric membrane for a period of time. Some dust particles have chemicals adsorbed to their surfaces. When these dust particles contact and adhere to the elastomeric membrane, the chemicals can be desorbed from the dust particles and can pass through the elastomeric membrane for sampling. In one embodiment, the desorbtion of the chemicals from the dust particles can be enhanced though heating of the elastomeric membrane. As the dust is heated, chemicals that were adsorbed from the air into the dust can diffuse through the membrane. As discussed above, passage of air flow over the elastomeric membrane at high velocity can facilitate removal of dust that has adhered to the membrane. This removal of particulates cleans the elastomeric membrane and reduces buildup of dust particulates which might impede the transfer of chemicals from the air.

In another embodiment, a mechanical wiper 17 type device may be used to physically wipe dust buildup off of the elastomeric membrane. The process of wiping the dust off the membrane may be a dry process or a wet process. For example, a wetting substance such as deionized water can be used in conjunction with the mechanical wiper 17 to wash the dust off of the membrane. However, a dry wiping process can be used in a less complex system and may be advantageous since wetting dust material can cause undesired clumping of the dust.

When a new elastomeric membrane is used or a system is turned on for the first time, the rate of adherence of particles in the airflow which adhere to the membrane may be higher then the rate at which the particles are displaced or blown off the elastomeric membrane. The membrane will eventually reach a substantially steady state, wherein the number of particulates that adhere to and are removed from the membrane due to the air flow will be substantially equal. The ability to sense the additional chemical content transferred from dust particulates in the air can provide a more accurate and sensitive sample of chemicals that are present in the air. Systems that attempt to filter dust prior to sampling the chemicals in the air can remove a significant portion of chemicals that are available for sampling.

In some situations, it may be disadvantageous to sample chemicals present in the dust particulates in the air. In these situations, the composition of the elastomeric membrane can be selected to minimize adhesion of the dust to its surface. In one embodiment, the support structure for the elastomeric membrane can include a cleaning component which can be configured to wipe or displace any dust which might have accumulated on the surface of the elastomeric membrane. The frequency of the cleaning by the cleaning component can be controlled dependent on various factors such as the quantity of dust in the air, the velocity of the air intake, the air humidity, the types of chemicals being sampled, etc. Additionally, the systems of the present invention can be used in combination with known particulate filtering techniques which can be disposed prior to the elastomeric membrane in order to remove large dust particles. The membrane can then be used to filter relatively small particulate matter, such as dust particles having a size less then 50 microns. This enables the chemical sampling device to be substantially free of dust contamination, including small particulates that typically escape filters and cyclones.

Figure 3:
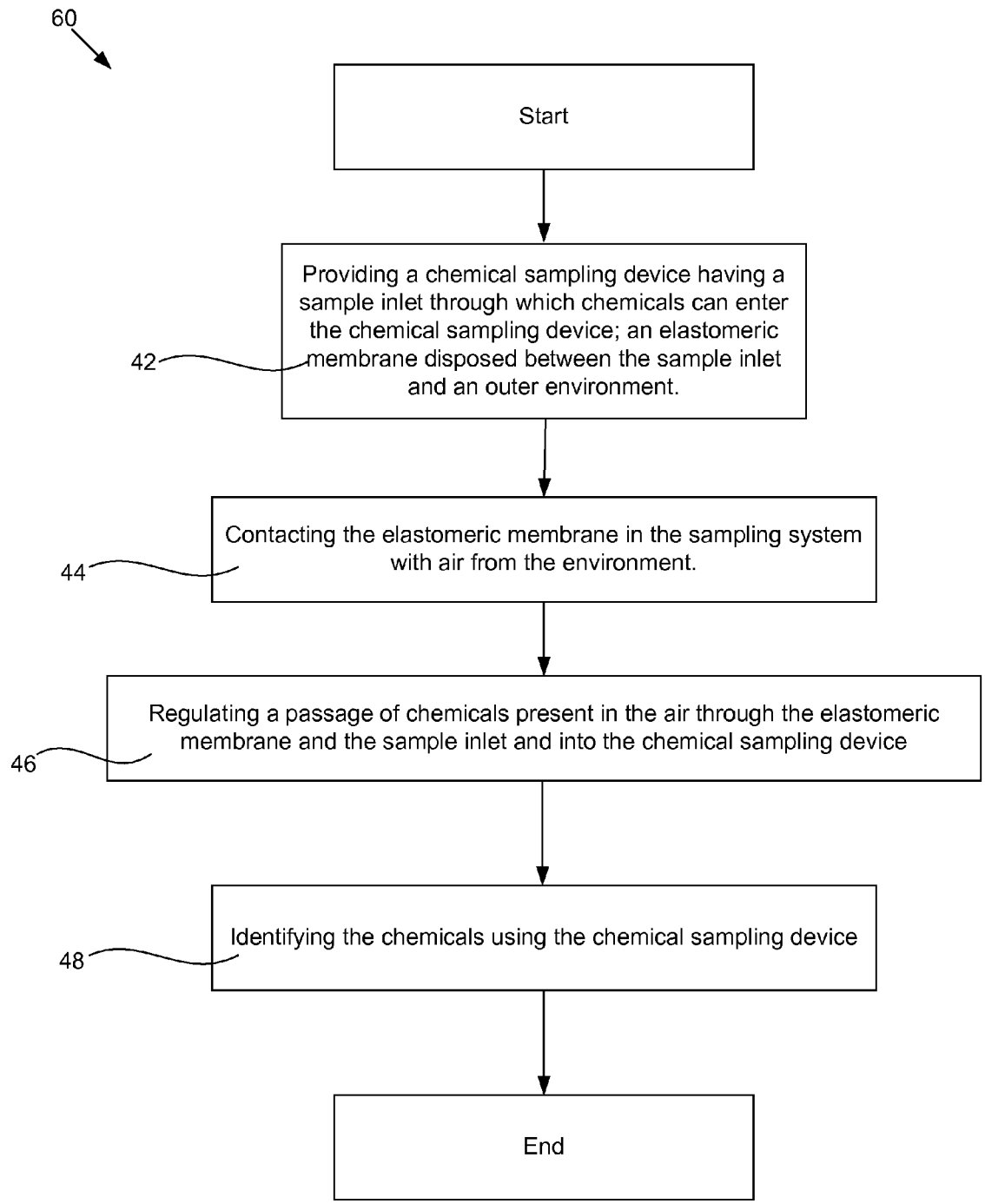
FIG. 3 is a schematic flow diagram illustrating one embodiment of a method of measuring atmospheric chemical composition in accordance with the present application.

In accordance with another embodiment of the present invention, a method 60 of measuring atmospheric chemical composition is disclosed, as depicted in the schematic flow diagram of FIG. 3. A chemical sampling system can be used in the method. The chemical sampling system can include a chemical sampling device having a sample inlet, an elastomeric membrane which can be disposed between the sample inlet and the environment being tested. A support structure can be disposed between the elastomeric membrane and the sample inlet. The support structure can be configured to provide mechanical support to the elastomeric membrane.

The method 60 includes the steps of providing 42 providing a chemical sampling device having a sample inlet through which chemicals can enter the chemical sampling device. An elastomeric membrane is disposed between the sample inlet and an outer environment. A support structure is disposed between the elastomeric membrane and the sample inlet. The support structure is configured to provide mechanical support to the elastomeric membrane. The method further includes the step of contacting 44 the elastomeric membrane in the sampling system with air from the environment, regulating 46 the passage of chemicals present in air through the elastomeric membrane and the sample inlet and into the chemical sampling device, and identifying 48 the chemicals using the chemical sampling device.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A system for sampling chemicals from a gaseous environment, comprising:
a chemical detector, said detector having a sample inlet through which chemicals from the gaseous environment enter the chemical detector;
an elastomeric membrane disposed between the sample inlet and the gaseous environment, wherein the elastomeric membrane is configured to extract chemicals from the gaseous environment while excluding dust and other particles from the chemical detector;
an air inlet operably disposed between the elastomeric membrane and the gaseous environment, wherein the air inlet includes a cyclone and the elastomeric membrane is integrated in a wall of the cyclone; and
a support structure disposed between the elastomeric membrane and the sample inlet, said support structure configured to provide mechanical support to the elastomeric membrane.

2. The system of claim 1, wherein the chemical detector is selected from the group consisting of a gas chromatograph, an ion mobility spectrometer, a mass spectrometer, a Raman spectrometer, and a point chemical detector.

3. The system of claim 1, wherein the air inlet is configured to pass air over the elastomeric membrane to cause accumulations of dust to be removed.

4. The system of claim 1, further comprising a wiper operable to remove dust buildup from the elastomeric membrane.

5. The system of claim 1, wherein the elastomeric membrane has a thickness of 0.001 inches to 0.5 inches.

6. The system of claim 1, wherein the elastomeric membrane is made from an elastomeric composition selected from the group consisting of silicone rubber, silastic, polyurethane, high density foam, and combinations thereof.

7. The system of claim 1, wherein the elastomeric membrane is silicone rubber.

8. The system of claim 1, wherein the support structure is made from a material selected from the group consisting of stainless steel, ceramic, plastic, and combinations thereof.

9. The system of claim 1, wherein the support structure is configured to heat the elastomeric membrane.

10. The system of claim 9, wherein the support structure is configured as a Peltier heater.

11. The system of claim 9, wherein the support structure is configured to heat the elastomeric membrane to a temperature range of 35° C. to 500° C.

12. A method of measuring atmospheric chemical composition, comprising:
providing a chemical sampling device having a sample inlet through which chemicals can enter the chemical sampling device; an elastomeric membrane disposed between the sample inlet and an outer environment and an air inlet including a cyclone having the elastomeric membrane integrated into a wall thereof, and a support structure disposed between the elastomeric membrane and the sample inlet, said support structure configured to provide mechanical support to the elastomeric membrane;

contacting the elastomeric membrane with air from the environment;

regulating a passage of chemicals present in the air through the elastomeric membrane and the sample inlet and into the chemical sampling device; and identifying the chemicals using the chemical sampling device.

13. The method of claim 12, wherein regulating the passage of chemicals further comprises heating the elastomeric membrane to facilitate the passage of the chemicals into the chemical sampling device.

14. The method of claim 13, wherein heating of the elastomeric membrane further comprises heating the elastomeric membrane to a temperature of 35° C. to 500° C.

15. The method of claim 12, wherein regulating the passage of chemicals further comprises cooling the elastomeric membrane to inhibit the passage of chemicals into the gas chromatograph.

16. The method of claim 15, wherein cooling of the elastomeric membrane further comprises cooling the elastomeric membrane to a temperature of −100° C. to 50° C.

17. The method of claim 12, wherein contacting the elastomeric membrane with the air further comprises actively passing the air over the elastomeric membrane.

18. The method of claim 12, further comprising passing the air through a cyclone prior to the step of contacting the elastomeric membrane.

19. A system for sampling chemicals from a gaseous environment, comprising:

a chemical sampling device, said chemical sampling device having a sample inlet through which chemicals from the gaseous environment enter the chemical sampling device;

an elastomeric membrane covering said sample inlet; and an air inlet including a cyclone having the elastomeric membrane integrated into a wall thereof;

wherein the elastomeric membrane is configured to extract chemicals from the gaseous environment and collect dust particles from the gaseous environment and allow chemicals adsorbed in the dust particles to transfer through the elastomeric membrane and into the chemical sampling device; and a support structure disposed between the elastomeric membrane and the sample inlet, said support structure configured to provide mechanical support to the elastomeric membrane.

* * * * *